United States Patent [19]
Poetsch et al.

[11] Patent Number: 5,723,682
[45] Date of Patent: Mar. 3, 1998

[54] DIFLUOROVINYL ETHERS

[75] Inventors: Eike Poetsch, Mühltal; Werner Binder, Dieburg; Michael Kompter, Riedstadt; Joachim Krause, Dieburg; Kazuaki Tarumi, Seeheim-Jugenheim; Ekkehard Bartmann, Erzhausen, all of Germany

[73] Assignee: Merck Patent Gesellschaft mit Beschrankter Haftung, Darmstadt, Germany

[21] Appl. No.: 812,335

[22] Filed: Mar. 5, 1997

[30] Foreign Application Priority Data

Mar. 6, 1996 [DE] Germany .................. 196 08 634.5

[51] Int. Cl.⁶ .................................................. C07C 41/16
[52] U.S. Cl. .................. 568/655; 568/663; 568/669; 568/670; 252/299.01; 252/299.63; 252/299.66
[58] Field of Search .................. 568/663, 669, 568/670, 655; 252/299.63, 299.66, 299.01

[56] References Cited

U.S. PATENT DOCUMENTS 4,877,548 10/1989 Kitano et al. .

OTHER PUBLICATIONS

Abstract of DE 42 38 377 Nov. 13, 1992.

*Primary Examiner*—Gary Geist
*Assistant Examiner*—Sreeni Padmanabhan
*Attorney, Agent, or Firm*—Millen, White, Zelano, & Branigan, P.C.

[57] ABSTRACT

The invention relates to difluorovinyl ethers of the general formula I

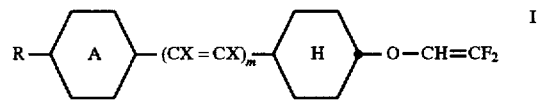

in which R, A, X and m are as defined in claim 1, and to the use of these compounds as components of liquid-crystalline media, and to liquid-crystal and electro-optical display elements which contain the novel liquid-crystalline media.

6 Claims, No Drawings

DIFLUOROVINYL ETHERS

The invention relates to difluorovinyl ethers of the general formula I

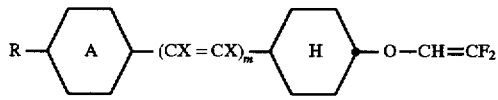

in which

R is alkyl or alkenyl having 1 to 12 carbon atoms, in each of which one or more $CH_2$ groups may be replaced by —O—, —$CF_2$— or —CH=CH—, a terminal $CH_3$— group may be replaced by $CF_3$—, a terminal $CH_2$—CH— group may be replaced by $CH_2$=CH— or $CH_2$=CF—, and one or two CH groups may be replaced by CF in such a way that two oxygen atoms are not linked to one another the ring A is 1,4-cyclohexylene, 1,4-cyclohexenylene or 1,4-phenylene, each of which is unsubstituted or substituted by 1 or 2 F atoms, each X is H or F, and m is 0 or 1.

The invention furthermore relates to the use of these compounds as components of liquid-crystalline media, and to liquid-crystal and electro-optical display elements which contain the novel liquid-crystalline media.

The compounds of the formula I can be used as components of liquid-crystalline media, in particular for displays based on the principle of the twisted cell, the guest-host effect, the effect of deformation of aligned phases or the effect of dynamic scattering.

Similar difluorovinyl ethers are disclosed, for example, in DE 42 38 377, but the difluorovinyl ether group in the compounds described therein is linked to an aromatic ring.

EP 0 325 796 describes liquid-crystalline compounds in which a cyclohexane ring is linked to a difluorovinyl group. However, these compounds have proven unstable and tend to decompose with elimination of HF.

The invention therefore had an object of finding novel, stable liquid-crystalline or mesogenic compounds which are suitable as components of liquid-crystalline media and in particular simultaneously have comparatively low viscosity and are stable to elevated temperatures and UV irradiation.

It has now been found that compounds of the formula I are eminently suitable as components of liquid-crystalline media. In particular, they have high nematogeneity and comparatively low viscosities. They can be used to obtain stable liquid-crystalline media having a broad mesophase range and advantageous values for the optical and dielectric anisotropy. These media furthermore have very good low-temperature behavior.

In addition, the provision of compounds of the formula I very generally considerably broadens the range of liquid-crystalline substances which are suitable, from various applicational points of view, for the preparation of liquid-crystalline mixtures.

The compounds of the formula I have a broad range of applications. Depending on the choice of the substituents, these compounds can be used as base materials of which liquid-crystalline media are predominantly composed; however, it is also possible to add compounds of the formula I to liquid-crystalline base materials from other classes of compounds in order, for example, to modify the dielectric and/or optical anisotropy of a dielectric of this type and/or to optimize its threshold voltage and/or its viscosity.

In the pure state, the compounds of the formula I are colorless and form liquid-crystalline mesophases in a temperature range which is favorably located for electro-optical use. They are stable chemically, thermally and to light.

The invention thus relates to compounds of the formula I and to the use of these compounds as components of liquid-crystalline media. The invention furthermore relates to liquid-crystalline media containing at least one compound of the formula I, and to liquid-crystal display elements, in particular electro-optical display elements, in particular STN (supertwisted nematic cell) displays, which contain media of this type.

The compounds of the formula I include the preferred compounds of the subformulae Ia to Ic:

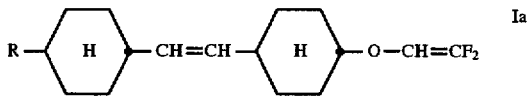

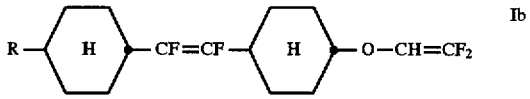

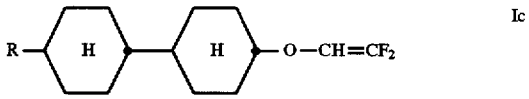

in which R is as defined above.

If R is an alkyl radical and/or an alkoxy radical, this may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, methoxy, octoxy, nonoxy, decoxy, undecoxy or dodecoxy.

Oxaalkyl, where a —$CH_2$— group is replaced by —O—, is preferably straight-chain 2-oxa-propyl (=methoxymethyl), 2-oxabutyl (=ethoxymethyl) or 3-oxabutyl (=2-methoxyethyl), 2-, 3- or 4-oxapentyl, 2- 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

If R is an alkenyl radical, this may be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl or dec-1-, -2-, -3-, -4-, -5-, -6-, -7-, -8- or -9-enyl. particular preference is given to the vinyl group and trans-alk-1-enyl radicals.

If R is an alkyl or alkenyl radical in which one or more $CH_2$ groups have been replaced by $CH_2$, this radical is preferably straight-chain. In the case of multiple substitution, the resultant radicals also include perfluorinated radicals. In the case of mono-substitution, the fluorine substituent can be in any desired position, but is preferably in the ω-position.

In a particularly preferred embodiment, R is $C_nH_{2n+1}$—(CH=CH)$_o$—, $CH_2$=CH—O or $CH_2$=CF—O—, n is from 1 to 8, and o is 0 or 1.

Compounds of the formula I containing branched wing groups R may occasionally be of importance owing to better solubility in the conventional liquid-crystalline base materials, but in particular as chiral dopants if they are optically active. Smectic compounds of this type are suitable as components of ferro-electric materials.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

The formula I covers the racemates of these compounds and the optical antipodes, and mixtures thereof.

Of these compounds of the formula I and of the subformulae, preference is given to those in which at least one of the radicals present therein has one of the preferred meanings indicated.

In the compounds of the formula I, preference is given to the stereoisomers in which the cyclohexane ring is trans-1, 4-disubstituted.

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for said reactions.

Use can also be made here of variants which are known per se, but are not described here in greater detail.

If desired, the starting materials can also be formed in situ, by not isolating them from the reaction mixture, but instead immediately converting them further into the compounds of the formula I.

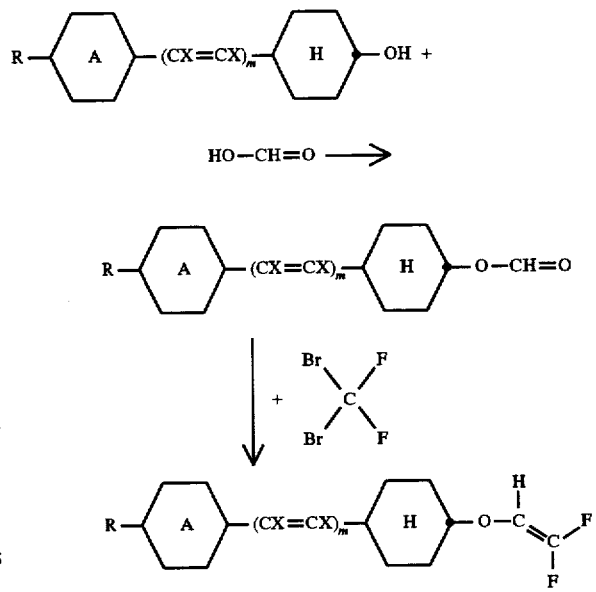

The novel compounds can be prepared simply, for example, in accordance with one of the following reaction schemes:

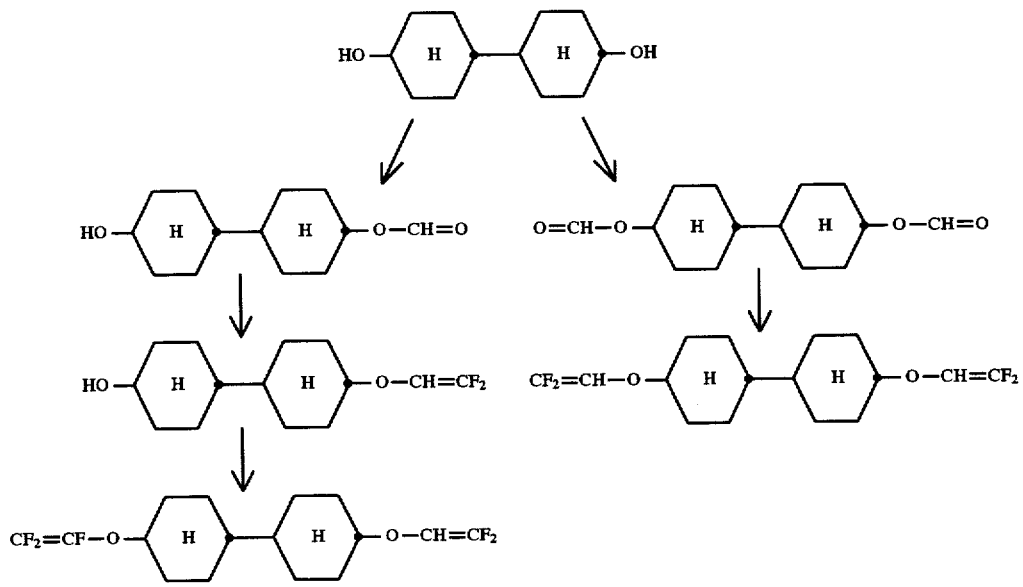

The intermediates needed to prepare the compounds of the formula I in which m is 1 can be prepared in accordance with Scheme 3:

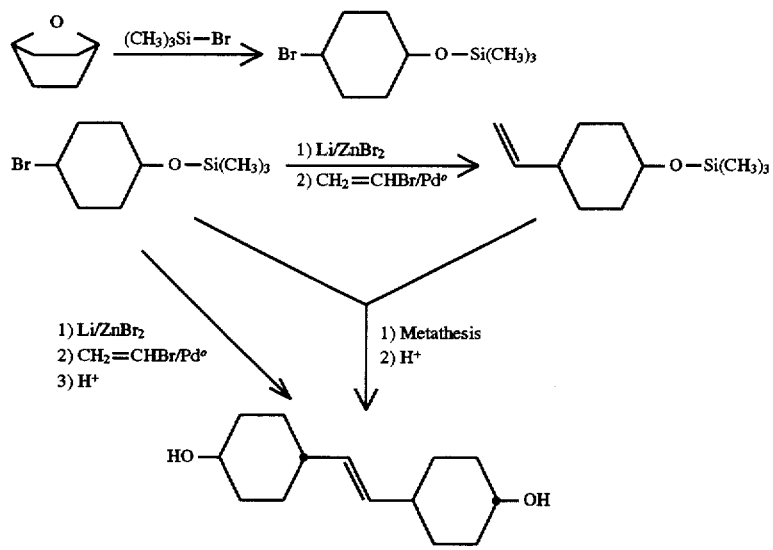

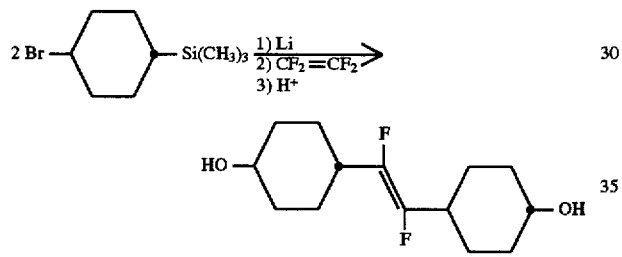

The novel liquid-crystalline media preferably contain 2 to 40, in particular 4 to 30, components as further constituents besides one or more novel compounds. These media very particularly preferably contain 7 to 25 components besides one or more novel compounds. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, trans-1,2-dicyclohexylethanes, 1-phenyl-2-cyclohexylethanes, 1-cyclohexyl-2-(4-phenylcyclohexyl)ethanes, trans-1-cyclohexyl-2-(4-phenylcyclohexyl)-ethenes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of novel media can be characterized by the formulae 1, 2, 3, 4, 5 and 6:

| | |
|---|---|
| R'—L—E—R" | 1 |
| R'—L—COO—E—R" | 2 |
| R'—L—OOC—E—R" | 3 |
| R'—L—C₂CH₂—E—R" | 4 |
| R'—L—C≡C—E—R" | 5 |
| R'—L—CH=CH—E—R" | 6 |

In the formulae 1, 2, 3, 4, 5 and 6, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

In the case of the compounds of the formula 6, the rings L and E directly linked to the CH=CH group are each -Cyc-.

One of the radicals L and E is preferably Cyc, Phe or Pyr. E is preferably Cyc, Phe or Phe-Cyc. The novel media preferably contain one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4, 5 and 6, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labelled with the sub-formulae 1a, 2a, 3a, 4a, 5a and 6a. In most of these compounds, R' and R" are different from one another, one of these radicals usually being alkyl, alkenyl, alkoxy or alkoxyalkyl.

In another smaller sub-group of the compounds of the formulae 1, 2, 3, 4, 5 and 6 which is known as group B, R" is —F, —Cl, —NCS or —(O)$_i$CH$_{3-(k+l)}$F$_k$Cl$_l$, where i is 0 or 1 and k+l is 1, 2 or 3; the compounds in which R" has this meaning are labelled with the sub-formulae 1b, 2b, 3b, 4b, 5b and 6b. Particular preference is given to those compounds of the sub-formulae 1b, 2b, 3b, 4b, 5b and 6b in which R" is —F, —Cl, —NCS, —CF$_3$, —OCHF$_2$ or —OCF$_3$.

In the compounds of the sub-formulae 1b, 2b, 3b, 4b, 5b and 6b, R' is as defined for the compounds of the sub-formulae 1a–6a and is preferably alkyl, alkenyl, alkoxy or alkoxyalkyl.

In a further, smaller sub-group of the compounds of the formulae 1, 2, 3, 4, 5 and 6, R" is —CN; this sub-group is known as group C below, and the compounds of this sub-group are correspondingly described by sub-formulae 1c, 2c, 3c, 4c, 5c and 6c. In the compounds of the sub-formulae 1c, 2c, 3c, 4c, 5c and 6c, R' is as defined for the compounds of the sub-formulae 1a–6a and is preferably alkyl, alkoxy or alkenyl.

In addition to the preferred compounds of groups A, B and C, other compounds of the formulae 1, 2, 3, 4, 5 and 6 having other variants of the proposed substituents are also customary. All these substances can be obtained by methods which are known from the literature or analogously thereto.

Besides novel compounds of the formula I, the novel media preferably contain one or more compounds selected from group A and/or group B and/or group C. The proportions by weight of the compounds from these groups in the novel media are preferably Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular novel media preferably being 5%–90% and in particular 60% to 90%.

The novel media preferably contain 1 to 40%, particularly preferably 5 to 30%, of the novel compounds of formula I. Further preferred media are those which contain more than 40%, in particular 45 to 70%, of the novel compounds of formula I. The media preferably contain one, two, three, four or five novel compounds of formula I.

The novel media are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. 196 08 634.5, filed Mar. 6, 1996 is hereby incorporated by reference.

EXAMPLES

In the present application and in the examples below, the structures of the liquid-crystal compounds are indicated by acronyms, the transformation into chemical formulae taking place as in Tables A and B below. All the radicals C$_n$H$_{2n+1}$ and C$_m$H$_{2m+1}$ are straight-chain alkyl radicals containing n or m carbon atoms respectively. The coding in Table B is self-evident. In Table A, only the acronym for the parent structure is given. In individual cases, the acronym for the parent structure is followed, separated by a hyphen, by a code for the substituents R$^1$, R$^2$, L$^1$, L$^2$ and L$^3$:

| Code for R$^1$, R$^1$ R$^2$, L$^1$, L$^2$ and L$^3$ | R$^2$ | L$^1$ | L$^2$ | L$^3$ |
|---|---|---|---|---|
| nm | C$_n$H$_{2n+1}$ | C$_m$H$_{2m+1}$ | H | H | H |
| nOm | C$_n$H$_{2n+1}$ | OC$_m$H$_{2m+1}$ | H | H | H |
| nO.m | OC$_n$H$_{2n+1}$ | C$_m$H$_{2m+1}$ | H | H | H |
| n | C$_n$H$_{2n+1}$ | CN | H | H | H |
| nN.F | C$_n$H$_{2n+1}$ | CN | H | F | H |
| nF | C$_n$H$_{2n+1}$ | F | H | H | H |
| nOF | OC$_n$H$_{2n+1}$ | F | H | H | H |
| nCl | C$_n$H$_{2n+1}$ | Cl | H | H | H |
| nF.F | C$_n$H$_{2n+1}$ | F | H | F | H |
| nCF$_3$ | C$_n$H$_{2n+1}$ | CF$_3$ | H | H | H |
| nOCF$_3$ | C$_n$H$_{2n+1}$ | OCF$_3$ | H | H | H |
| nOCF$_2$ | C$_n$H$_{2n+1}$ | OCHF$_2$ | H | H | H |
| nS | C$_n$H$_{2n+1}$ | NCS | H | H | H |
| rVsN | C$_r$H$_{2r+1}$—CH=CH—C$_s$H$_{2s}$— | CN | H | H | H |
| nOmFF | C$_n$H$_{2n+1}$ | OC$_m$H$_{2m+1}$ | F | F | H |
| nF.F.F | C$_n$H$_{2n+1}$ | F | F | H | F |
| n-OXF | C$_n$H$_{2n+1}$ | OCH=CF$_2$ | H | H | H |
| nOCF$_3$.F.F | C$_n$H$_{2n+1}$ | OCF$_3$ | F | H | F |

Table A:

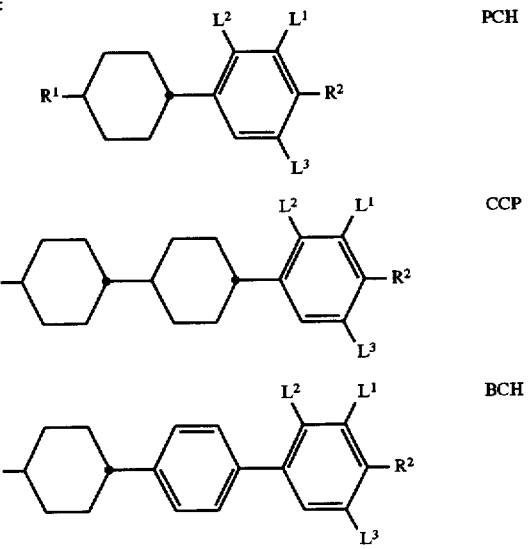

Table A:

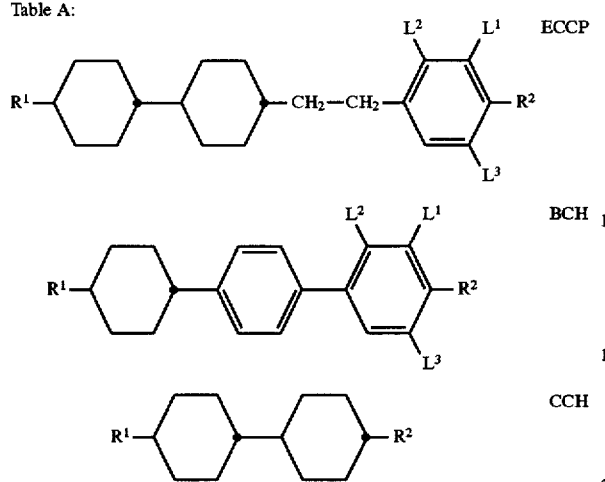

Table B:

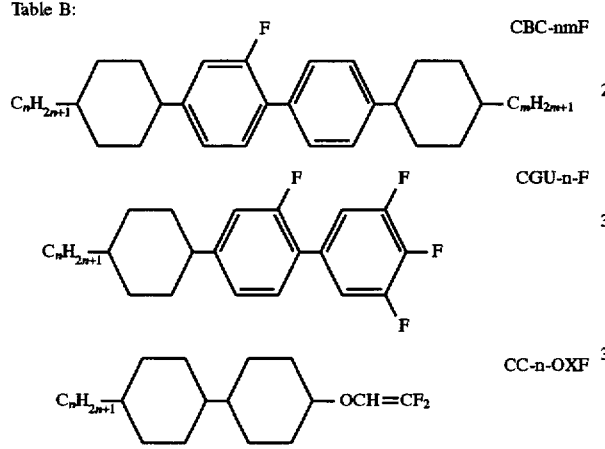

The examples below are intended to illustrate the invention without representing a limitation. Above and below, percent data are percent by weight. All temperatures are given in degrees Celsius. mp.=melting point, cp.=clearing point. Furthermore, C=crystal-line state, N=nematic phase, S=smectic phase and I=isotropic phase. The numbers between these symbols indicate the conversion temperature. Δn denotes optical anisotropy (589 nm, 20° C.), and the viscosity (mm²/sec) was determined at 20° C.

"Conventional work-up" means that water is added if necessary, the mixture is extracted with dichloromethane, diethyl ether or toluene, the organic phase is separated off, dried and evaporated, and the product is purified by distillation under reduced pressure or crystallization and/or chromatography. The following abbreviations are used:

DMEU 1,3-dimethyl-2-imidazolidinone
POT potassium tertiary-butanolate
THF tetrahydrofuran
pTsOH p-toluenesulfonic acid
HMPT hexamethyl triaminophosphite
DMAP 4-(N,N-dimethylamino)pyridine
DCC dicyclohexylcarbodiimide

Example 1

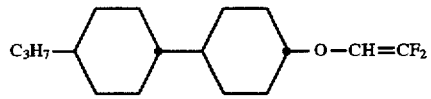

Step 1.1

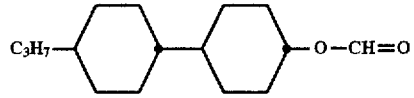

1A

A mixture of 0.5 mol (18.9 ml) of formic acid and 250 ml of dichloromethane is added dropwise at −5° C. to a mixture of 0.5 mol (106.1 g) of trans,trans-4-n-propyl-4'-hydroxybicyclohexyl and 500 ml of dichloromethane. A mixture of 0.05 mol (6.1 g) of DMAP, 0.6 mol (123.8 g) of DCC and 250 ml of dichloromethane is then added. The mixture is stirred at room temperature for 14 hours and subjected to conventional work-up, giving 93.7 g (74.2% of theory) of 1A.

Step 1.2

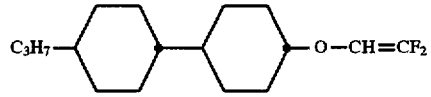

1B 0.15 mol of dibromodifluoromethane and 0.3 mol of HMPT are added successively at 5° C. to a mixture of 0.075 mol of 1A, 30 ml of THF and 300 ml of 1,4-dioxane. The mixture is stirred at room temperature for 14 hours and subjected to conventional work-up, giving 9.0 g (41.9% of theory) of 1B, C 30 N (13.2) I; Δn=+0.037; Δε=+3.73.

The following compounds of the formula

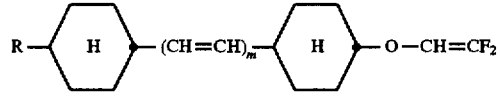

are prepared analogously:

| R | m | |
|---|---|---|
| $C_2H_5$ | 0 | C −6 I; Δn = −0.071; Δε = −5.41 |
| n-$C_4H_9$ | 0 | |
| n-$C_5H_{11}$ | 0 | C 34 N (31) I; Δn = +0.045; Δε = +4.55 |
| $CH_2$=CH— | 0 | |
| $CH_3$—CH=CH— | 0 | |
| $C_2H_5$ | 1 | |
| n-$C_3H_7$ | 1 | |
| n-$C_4H_9$ | 1 | |
| n-$C_5H_{11}$ | 1 | |
| $CH_2$=CH— | 1 | |
| $CH_3$—CH=CH— | 1 | |

The examples below relate to liquid-crystalline mixtures containing compounds of the formula I:

Example A

| | | |
|---|---|---|
| PCH-5F | 9.0% | Clearing point: 85° C. |
| PCH-6F | 7.2% | Δn (20° C.; 589 nm): +0.0921 |
| PCH-7F | 5.4% | $v_{20°\,C.}$: 14.0 mm²/s |
| CCP-2OCF$_3$ | 7.2% | Δε (20° C.; 1 kHz): +5.86 |
| CCP-3OCF$_3$ | 10.8% | |
| CCP-4OCF$_3$ | 8.1% | |
| CCP-5OCF$_3$ | 8.1% | |
| BCH-3F.F | 10.8% | |
| BCH-5F.F | 9.0% | |
| ECCP-3OCF$_3$ | 4.5% | |
| ECCP-5OCF$_3$ | 4.5% | |
| CBC-33F | 1.8% | |
| CBC-53F | 1.8% | |
| CBC-55F | 1.8% | |
| CC-5-OXF | 10.0% | |

Example B

| | | |
|---|---|---|
| PCH-5F | 9.0% | Clearing point: 83° C. |
| PCH-6F | 7.2% | Δn (20° C.; 589 nm): 0.0920 |
| PCH-7F | 5.4% | $v_{20°\,C.}$: 13.7 mm²/s |
| CCP-2OCF$_3$ | 7.2% | Δε (20° C.; 1 kHz): +5.75 |
| CCP-3OCF$_3$ | 10.8% | |
| CCP-4OCF$_3$ | 8.1% | |
| CCP-5OCF$_3$ | 8.1% | |
| BCH-3F.F | 10.8% | |
| BCH-5F.F | 9.0% | |
| ECCP-3OCF$_3$ | 4.5% | |
| ECCP-5OCF$_3$ | 4.5% | |
| CBC-33F | 1.8% | |
| CBC-53F | 1.8% | |
| CBC-55F | 1.8% | |
| CC-3-OXF | 10.0% | |

Example C

| | | |
|---|---|---|
| PCH-5F | 9.0% | Clearing point: 61.2° C. |
| PCH-6F | 7.2% | Δn (20° C.; 589 nm): +0.0806 |
| PCH-7F | 5.4% | $v_{20°\,C.}$: 15 mm²/s |
| CCP-2OCF$_3$ | 7.2% | Δε (20° C.; 1 kHz): +5.13 |
| CCP-3OCF$_3$ | 10.8% | |
| CCP-4OCF$_3$ | 8.1% | |
| CCP-5OCF$_3$ | 8.1% | |
| BCH-3F.F | 10.8% | |
| BCH-5F.F | 9.0% | |
| ECCP-3OCF$_3$ | 4.5% | |
| ECCP-5OCF$_3$ | 4.5% | |
| CBC-33F | 1.8% | |
| CBC-53F | 1.8% | |
| CBC-55F | 1.8% | |
| CC-2-OXF | 10.0% | |

Example D

| | | |
|---|---|---|
| CC-3-OXF | 8.0% | Clearing point: +89° C. |
| CC-5-OXF | 10.0% | Δn (589 nm; 20° C.): +0.0721 |
| CCH-34 | 5.0% | $V_{(10,0,20)}$: 1.80 V |
| CCH-35 | 5.0% | |
| CCP-2OCF$_3$ | 8.0% | |
| CCP-3OCF$_3$ | 8.0% | |
| CCP-4OCF$_3$ | 8.0% | |
| CCP-5OCF$_3$ | 8.0% | |
| CCP-2F.F.F | 12.0% | |
| CCP-3F.F.F | 12.0% | |
| CCP-5F.F.F | 8.0% | |
| ECCP-3F.F | 8.0% | |

Example E

| | | |
|---|---|---|
| CC-3-OXF | 5.0% | Clearing point: 92° C. |
| CC-5-OXF | 8.0% | Δn (589 nm; 20° C.): +0.0816 |
| CCP-2OCF$_3$ | 8.0% | Δε (1 kHz, 20° C.): +7.7 |
| CCP-3OCF$_3$ | 8.0% | $V_{(10,0,20)}$: 1.53 V |
| CCP-4OCF$_3$ | 8.0% | $K_3/K_1$: 1.83 |
| CCP-5OCF$_3$ | 8.0% | |
| CCP-2F.F.F | 12.0% | |
| CCP-3F.F.F | 12.0% | |
| CCP-5F.F.F | 8.0% | |
| CGU-3-F | 6.0% | |
| ECCP-3F.F | 6.0% | |
| CCP-3OCF$_2$.F.F | 11.0% | |

Example F

| | | |
|---|---|---|
| CC-3-OXF | 8.0% | Clearing point: +86° C. |
| CC-5-OXF | 8.0% | Δn (589 nm; 20° C.): +0.0745 |
| CCH-34 | 5.0% | Δε (1 kHz, 20° C.): +6.9 |
| CCH-35 | 5.0% | $V_{(10,0,20)}$: 1.62 V |
| CCP-2OCF$_3$ | 9.0% | $K_3/K_1$: 1.32 |
| CCP-3OCF$_3$ | 8.0% | |
| CCP-4OCF$_3$ | 6.0% | |
| CCP-5OCF$_3$ | 8.0% | |
| CCP-2F.F.F | 11.0% | |
| CCP-3F.F.F | 12.0% | |
| CCP-5F.F.F | 7.0% | |
| CGU-3-F | 4.0% | |
| CCP-3OCF$_2$.F.F | 9.0% | |

Example G

| | | |
|---|---|---|
| CC-3-OXF | 10.0% | Clearing point: +84° C. |
| CC-5-OXF | 9.0% | Δn (589 nm; 20° C.): +0.0704 |
| PCH-7F | 2.0% | Δε (1 kHz, 20° C.): +6.2 |
| CCH-34 | 6.0% | $V_{(10,0,20)}$: 1.77 V |
| CCH-35 | 6.0% | $K_3/K_1$: 1.28 |
| CCP-2OCF$_3$ | 10.0% | |
| CCP-3OCF$_3$ | 8.0% | |
| CCP-4OCF$_3$ | 5.0% | |
| CCP-5OCF$_3$ | 9.0% | |
| CCP-2F.F.F | 10.0% | |
| CCP-3F.F.F | 12.0% | |
| CCP-5F.F.F | 6.0% | |
| CCP-5OCF$_2$.F.F | 7.0% | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A difluorovinyl ether of the formula I

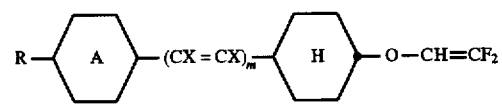

in which

R is alkyl or alkenyl having 1 to 12 carbon atoms, in each of which one or more CH$_2$ groups may be replaced by —O—, —CF$_2$— or —CH=CH—, a terminal CH$_3$— group may be replaced by CF$_3$—, a terminal CH$_2$—

CH— group may be replaced by $CH_2=CH-$ or $CH_2=CF-$, and one or two CH groups may be replaced by CF in such a way that two oxygen atoms are not linked to one another, the ring A is 1,4-cyclohexylene, 1,4-cyclohexenylene or 1,4-phenylene, each of which is unsubstituted or substituted by 1 or 2 F atoms, each X is H or F, and m is 0 or 1.

2. A difluorovinyl ether according to claim 1, selected from the formulae Ia, Ib and Ic:

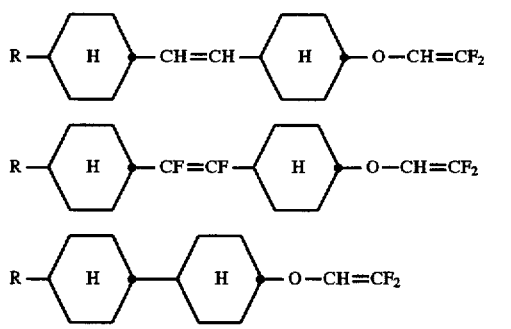

in which R is as defined.

3. A difluorovinyl ether according to claim 1 wherein

R is $C_nH_{2n+1}-(CH=CH)_o-$, $CH_2=CH-O$ or $CH_2=CF-O-$, n is from 1 to 8, and o is 0 or 1.

4. A method for improving the response time of an STN display, which comprises including a compound of the formula I of claim 1 in a liquid crystalline medium for the display.

5. A liquid crystalline medium having at least two liquid-crystalline components, wherein at least one component is a difluorovinyl ether of the formula I according to claim 1.

6. An electro-optical display, comprising as dielectric a medium according to claim 5.

* * * * *